United States Patent
Srivari et al.

(10) Patent No.: US 11,072,583 B2
(45) Date of Patent: Jul. 27, 2021

(54) INDOLE (SULFOMYL) N-HYDROXY BENZAMIDE DERIVATIVES AS SELECTIVE HDAC INHIBITORS

(71) Applicant: COUNCIL OF SCIENTIFIC & INDUSTRIAL RESEARCH, New Delhi (IN)

(72) Inventors: Chandrasekhar Srivari, Telangana (IN); Prathama Satyendra Mainkar, Telangana (IN); Chada Raji Reddy, Telangana (IN); Srigiridhar Kotamraju, Telangana (IN); Pavan Kumar Togapur, Telangana (IN); Subbarao Mohan Venkata Muppidi, Telangana (IN); Somesh Sharma, Telangana (IN); Ashok Kumar Jha, Telangana (IN); Prem Kumar Arumugam, Telangana (IN)

(73) Assignee: COUNCIL OF SCIENTIFIC & INDUSTRIAL RESEARCH, New Delhi (IN)

( * ) Notice: Subject to any disclaimer, the term of this patent is extended or adjusted under 35 U.S.C. 154(b) by 0 days.

(21) Appl. No.: 16/767,389

(22) PCT Filed: Aug. 6, 2018

(86) PCT No.: PCT/IN2018/050514
§ 371 (c)(1),
(2) Date: May 27, 2020

(87) PCT Pub. No.: WO2019/102488
PCT Pub. Date: May 31, 2019

(65) Prior Publication Data
US 2020/0385349 A1    Dec. 10, 2020

(30) Foreign Application Priority Data
Nov. 27, 2017 (IN) .............................. 201711042426

(51) Int. Cl.
C07D 209/40 (2006.01)
B01J 31/24 (2006.01)

(52) U.S. Cl.
CPC ........ *C07D 209/40* (2013.01); *B01J 31/2409* (2013.01); *B01J 2231/4211* (2013.01); *B01J 2531/824* (2013.01)

(58) Field of Classification Search
None
See application file for complete search history.

(56) References Cited

U.S. PATENT DOCUMENTS

| | | |
|---|---|---|
| 3,186,992 A | 6/1965 | Hoefle |
| 5,804,593 A | 9/1998 | Warpehoski et al. |
| 5,962,481 A | 10/1999 | Levin et al. |
| 6,437,177 B1 | 8/2002 | Warpehoski et al. |
| 6,469,043 B1 | 10/2002 | Haneda et al. |
| 6,548,524 B2 | 4/2003 | Levin et al. |
| 6,583,318 B2 | 6/2003 | Campian et al. |
| 7,183,298 B2 | 2/2007 | Watkins et al. |
| 2004/0092598 A1 | 5/2004 | Watkins et al. |
| 2004/0198830 A1 | 10/2004 | Watkins et al. |
| 2005/0085515 A1 | 4/2005 | Watkins et al. |
| 2005/0107445 A1 | 5/2005 | Watkins et al. |
| 2007/0004806 A1 | 1/2007 | Kalvinsh et al. |

FOREIGN PATENT DOCUMENTS

| | | |
|---|---|---|
| CN | 1380288 | 11/2002 |
| EP | 0977745 | 2/2000 |
| JP | 2000500145 A | 1/2011 |
| WO | WO 9816520 A1 | 4/1998 |
| WO | WO 9831664 A1 | 7/1998 |
| WO | WO 98/39313 A1 | 9/1998 |
| WO | WO 02/30879 A2 | 4/2002 |
| WO | WO 2006/017214 A2 | 2/2006 |
| WO | WO 2008/074132 A1 | 6/2008 |
| WO | WO 2009/040517 A2 | 4/2009 |

OTHER PUBLICATIONS

International Search Report and Written Opinion, PCT/IN2018/050514, dated Oct. 8, 2018.

*Primary Examiner* — Joseph R Kosack
(74) *Attorney, Agent, or Firm* — Knobbe, Martens, Olson & Bear, LLP

(57) ABSTRACT

Sulfonyl hydroxamic acid compounds have the following general formula:

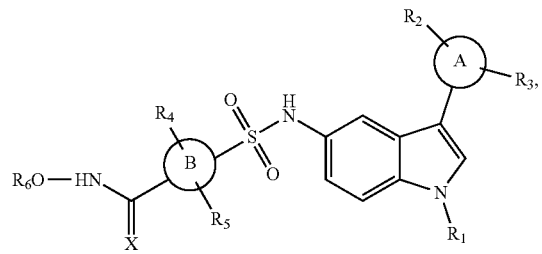

Ring A and B are aryl, heteroaryl, cycloalkyl, fused aryl or fused alkyl group, and $R_1$, $R_2$, $R_3$, $R_4$, $R_5$, and $R_6$ are hydrogen, alkoxy, aryloxy, hydroxy, ester, amide, amino, alkyl, aryl, heteroaryl, halogen, hydroxy, alkoxy, aryloxy, nitro, cyano, ester, or aldehyde. The compounds are HDAC inhibitors. Processes can be used for preparation of these indole-based sulfonyl hydroxamic acid derivatives.

15 Claims, 3 Drawing Sheets

(a)

(b)

(c)

(d)

INDOLE (SULFOMYL) N-HYDROXY BENZAMIDE DERIVATIVES AS SELECTIVE HDAC INHIBITORS

FIELD OF THE INVENTION

The present invention relates to sulfonyl hydroxamic acids as selective HDAC inhibitors. Particularly the present invention relates to indole based sulfonyl hydroxamic acid compounds of general formula I.

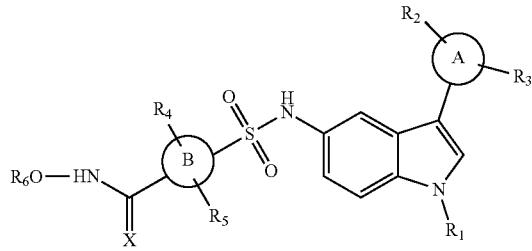

wherein
Ring A and B is aryl or heteroaryl or cycloalkyl or fused aryl or fused alkyl group $R_1$, $R_2$, $R_3$, $R_4$, $R_5$, $R_6$ is hydrogen, alkoxy, aryloxy, hydroxy, ester, amide, amino, alkyl, aryl, heteroaryl, halogen, hydroxy, alkoxy, aryloxy, nitro, cyano, ester, aldehyde.

BACKGROUND OF THE INVENTION

Sulfonyl hydroxamic acids are important structural motifs among a series of various pharmaceutically effective substances. These compounds were found to exhibit wide range of biological properties. (EP0977745; JP2000500145; U.S. Pat. Nos. 3,186,992; 5,804,593; 5,962,481; 6,437,177; 6,548,524; 6,583,318; WO9816520; WO9831664; WO2009040517; CN1380288). There are certain class of sulfonyl hydroxamic acid derivatives that are reported to exhibit HDAC inhibition properties (U.S. Pat. No. 7,183,298; US2004092598; US2004198830; US2005085515; US2005107445; US2007004806; WO0230879); however the compounds showing selective HDAC inhibition are very rarely noticed. Therefore the design and development of sulfonyl hydroxamic acids that are capable of selective HDAC inhibition properties is quiet challenging and the most required task. Although many types of sulfonyl hydroxamic acid derivatives were reported using a variety of strategies toward the construction of sulfonyl hydroxamic acid architecture, there are certain groups of sulfonyl hydroxamic acid derivatives of interest that have not been synthesized and evaluated for biological properties. Indole based sulfonyl hydroxamic acid derivatives of this invention are examples of this kind and are of rare occurrence. Therefore, there is a need for the development of methods for the synthesis and biological evaluation of diversely substituted indole based sulfonyl hydroxamic acid compounds. In this direction, this invention aims towards the synthesis and systematic screening of the structurally diverse sulfonyl hydroxamic acids based on indole core.

In this context a large number of new sulfonyl hydroxamic acid derivatives have been synthesized and evaluated for HDAC inhibition activity.

OBJECTIVE OF THE INVENTION

The main objective of the present invention is to provide novel sulfonyl hydroxamic acid derivatives as useful HDAC inhibitors.

The main objective of the present invention is to provide novel sulfonyl hydroxamic acid derivatives as useful selective HDAC inhibitors.

Another objective of the present invention is to provide the process for the preparation of novel sulfonyl hydroxamic acid derivatives.

SUMMARY OF THE INVENTION

The above and other objectives of the present invention are achieved by providing the new sulfonyl hydroxamic acid compounds, which have been synthesized and tested for the activity.

Accordingly, the present invention affords a new class of sulfonyl hydroxamic acid derivatives of general formula I.

Formula I

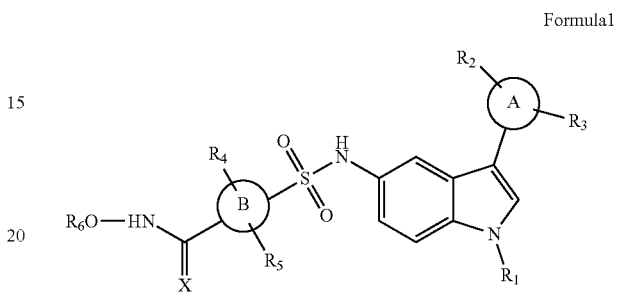

Wherein
Ring A and B is aryl or heteroaryl or cycloalkyl or fused aryl or fused alkyl group $R_1$, $R_2$, $R_3$, $R_4$, $R_5$, $R_6$ is hydrogen, alkoxy, aryloxy, hydroxy, ester, amide, amino, alkyl, aryl, heteroaryl, halogen, hydroxy, alkoxy, aryloxy, nitro, cyano, ester, aldehyde.

The structural formulas of the representative compounds are

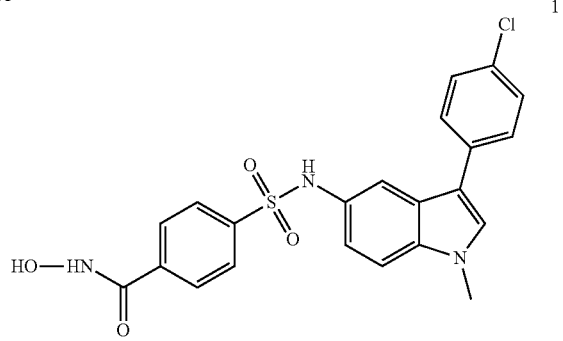

1

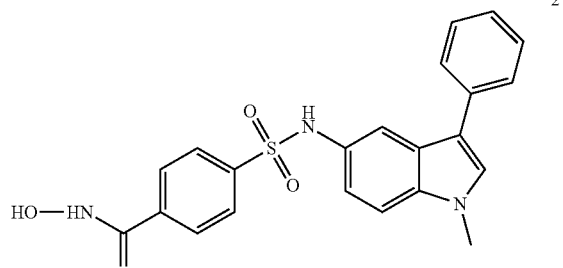

2

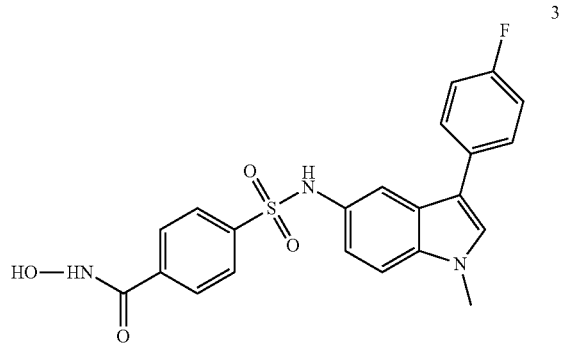

3

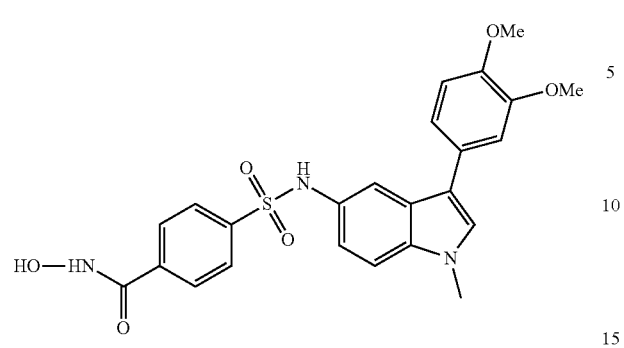
4
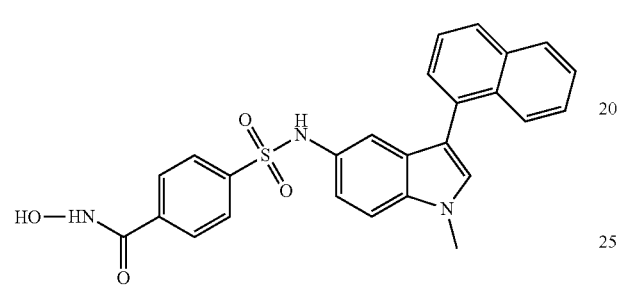
5
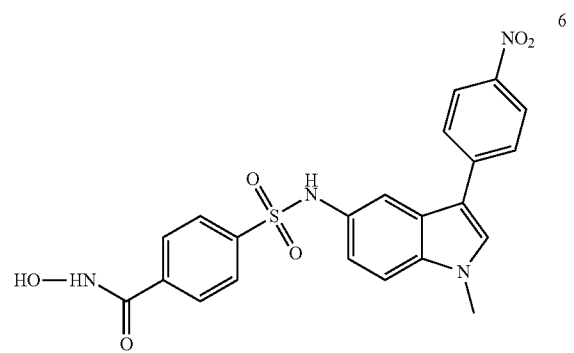
6
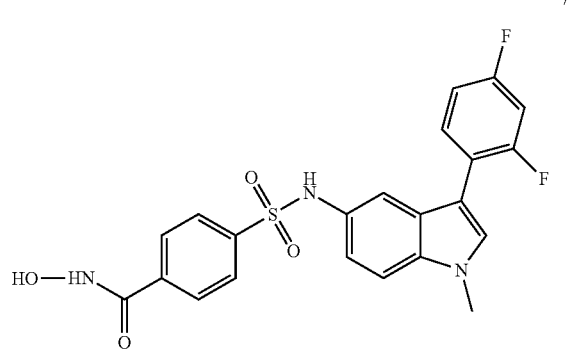
7
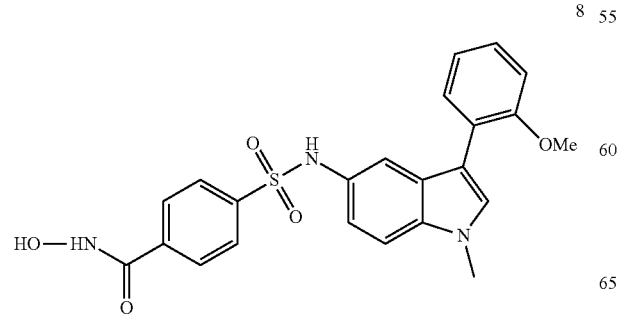
8
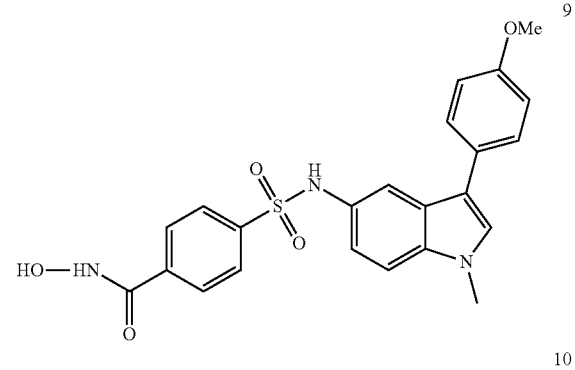
9
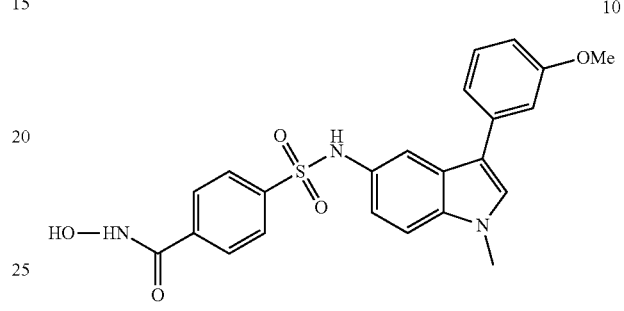
10
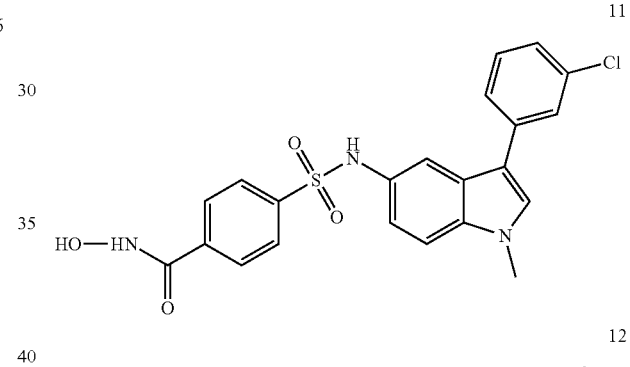
11
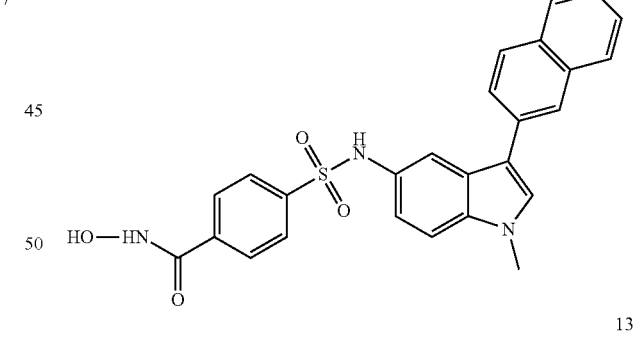
12
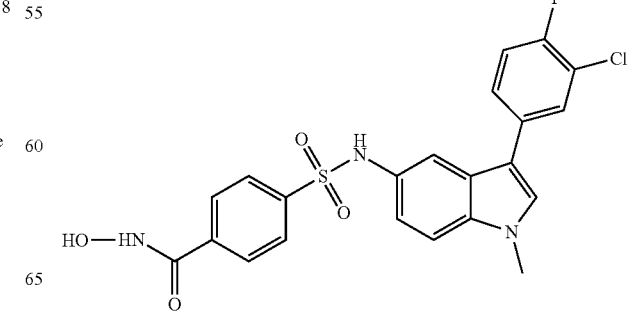
13

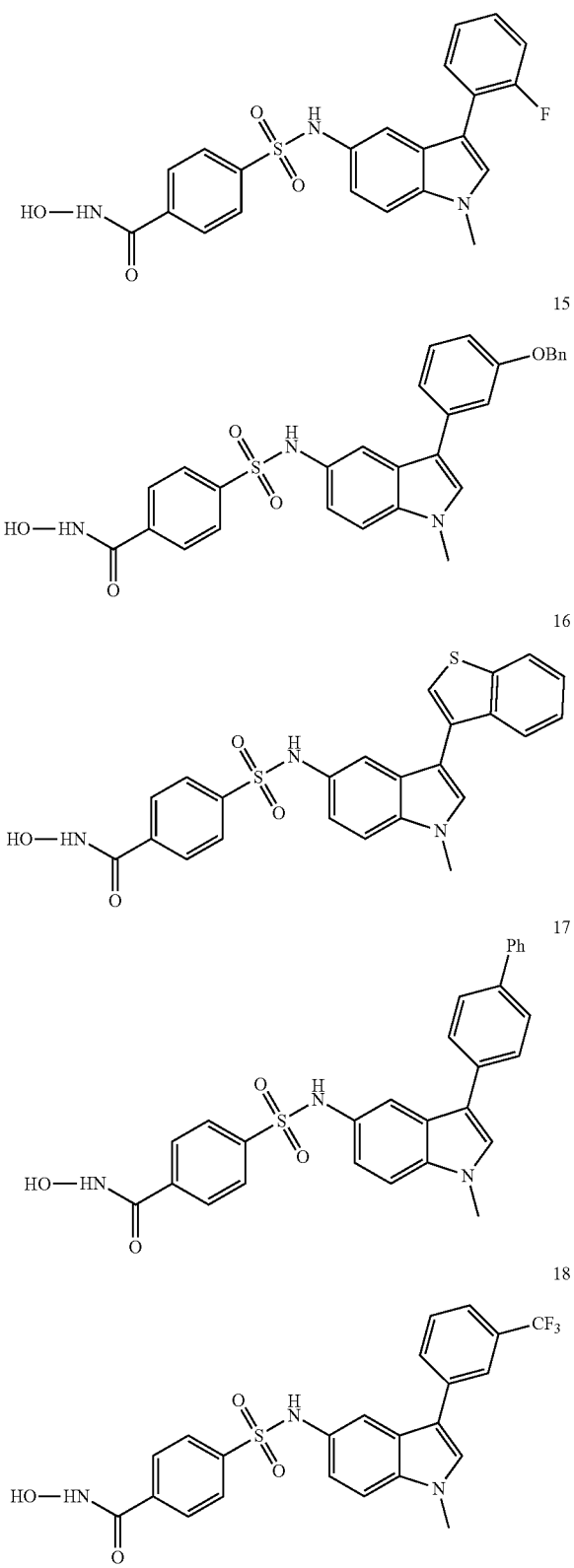

In an embodiment of the present invention, the novel sulfonyl hydroxamic acid derivatives described herein are represented by N-hydroxy-4-(N-(1-methyl-3-phenyl-1H-indol-5-yl)sulfamoyl)benzamide (1)
4-(N-(3-(4-chlorophenyl)-1-methyl-1H-indol-5-yl)sulfamoyl)-N-hydroxybenzamide (2)
4-(N-(3-(4-fluorophenyl)-1-methyl-1H-indol-5-yl)sulfamoyl)-N-hydroxybenzamide (3)
4-(N-(3-(3,4-dimethoxyphenyl)-1-methyl-1H-indol-5-yl)sulfamoyl)-N-hydroxy benzamide (4)
N-hydroxy-4-(N-(1-methyl-3-(naphthalen-1-yl)-1H-indol-5-yl)sulfamoyl)benzamide (5)
N-hydroxy-4-(N-(1-methyl-3-(4-nitrophenyl)-1H-indol-5-yl)sulfamoyl)benzamide (6)
4-(N-(3-(2,4-difluorophenyl)-1-methyl-1H-indol-5-yl)sulfamoyl)-N-hydroxybenzamide (7)
N-hydroxy-4-(N-(3-(2-methoxyphenyl)-1-methyl-1H-indol-5-yl)sulfamoyl)benzamide (8)
N-hydroxy-4-(N-(3-(4-methoxyphenyl)-1-methyl-1H-indol-5-yl)sulfamoyl)benzamide (9)
N-hydroxy-4-(N-(3-(3-methoxyphenyl)-1-methyl-1H-indol-5-yl)sulfamoyl)benzamide (10)
4-(N-(3-(3-chlorophenyl)-1-methyl-1H-indol-5-yl)sulfamoyl)-N-hydroxybenzamide (11)
N-hydroxy-4-(N-(1-methyl-3-(naphthalen-2-yl)-1H-indol-5-yl)sulfamoyl)benzamide (12)
4-(N-(3-(3-chloro-4-fluorophenyl)-1-methyl-1H-indol-5-yl)sulfamoyl)-N-hydroxybenzamide (13)
4-(N-(3-(2-fluorophenyl)-1-methyl-1H-indol-5-yl)sulfamoyl)-N-hydroxybenzamide (14)
4-(N-(3-(3-(benzyloxy)phenyl)-1-methyl-1H-indol-5-yl)sulfamoyl)-N-hydroxybenzamide (15)
4-(N-(3-(benzo[b]thiophen-3-yl)-1-methyl-1H-indol-5-yl)sulfamoyl)-N-hydroxybenzamide (16)
4-(N-(3-(biphenyl-4-yl)-1-methyl-1H-indol-5-yl)sulfamoyl)-N-hydroxybenzamide (17)
N-hydroxy-4-(N-(1-methyl-3-(3-(trifluoromethyl)phenyl)-1H-indol-5-yl)sulfamoyl) benzamide (18)

The present invention also provides a process for the preparation of sulfonyl hydroxamic acid derivatives as described in the above general formula:—

A large number of various sulfonyl hydroxamic acid derivatives possessing diversely substituted architecture were found to exhibit several biological properties. These functionalities are prominent structural motifs of new medicines from different pharmacological groups. The development of new structural scaffolds of sulfonyl hydroxamic acid architecture is very important for the drug discovery process. In this connection a large number of sulfonyl hydroxamic acid derivatives were developed as depicted in the above general formula I.

The process for the preparation of sulfonyl hydroxamic acid derivatives wherein the said process comprising the steps of:
a) bromination of nitroindole using brominating reagents in polar non-protonated solvents at −5 to 5° C. for 40-100 minutes;
b) protection of indole NH using alkyl halides and hydride base in polar non-protonated solvent at −5 to 5° C. for 40-100 minutes;
c) reduction of nitro group to amine using metal reducing reagent in polar solvent mixture at −5 to 5° C. for 40-100 minutes;
d) base mediated coupling between sulfonyl and amine functionalities in polar solvent at 25-40° C. for 12-24 hours;
e) suzuki reaction/coupling using boronic acid derivative, palladium catalyst and phosphate salt in polar solvent 70-100° C. for 5-10 hours;

f) installation of hydroxamic acid using hydroxy amine and a base in polar solvent mixture at 25-40° C. for 12-24 hours.

In yet another embodiment of the present invention, brominating reagent is selected from $Br_2$ or NBS.

In yet another embodiment of the present invention, polar non-protonated solvent is selected from DMF or DMSO.

In yet another embodiment of the present invention, alkyl halide is selected from methyl iodide, methyl bromide, ethyl iodide or ethyl bromide.

In yet another embodiment of the present invention, hydride base is selected from NaH, KH or CsH; metal reducing reagent is selected from Zn or Fe.

In yet another embodiment of the present invention, polar solvent/s are selected from THF, MeOH, EtOH, $H_2O$, $CH_3CN$, 1,4-dioxan or $Et_2O$.

In yet another embodiment of the present invention, base is selected from NaOH, KOH, CsOH, $NaHCO_3$ or $KHCO_3$.

In yet another embodiment of the present invention, boronic acid derivative is selected from aryl or heteroaryl or cycloalkyl or fused aryl or fused alkyl group with substitutions $R_1$ and/or $R_2$, where $R_1$ and/or $R_2$ is hydrogen, alkoxy, aryloxy, hydroxy, ester, amide, amino, alkyl, aryl, heteroaryl, halogen, hydroxy, alkoxy, aryloxy, nitro, cyano, ester or aldehyde.

In yet another embodiment of the present invention, palladium catalyst is selected from $Pd(PPh_3)_2Cl_2$ or $Pd(PPh_3)_4$; phosphate salt is selected from $K_3PO_4$ or $Na_3PO_4$.

In still another embodiment of the present invention the sulfonyl hydroxamic acid derivatives prepared are tested for their efficiency towards HDAC inhibition property.

Thus the present invention provides new class of sulfonyl hydroxamic acid derivatives which are useful as selective HDAC inhibitors. A program was initiated in the laboratory for the design and synthesis of novel sulfonyl hydroxamic acid derivatives, which can serve as new chemical entities for drug discovery process. In these efforts new sulfonyl hydroxamic acid derivatives have been synthesized and evaluated for HDAC activity. The synthesis of these compounds has been carried out as described in the following schemes using simple indole/oxindole analogues as the starting substrates.

DETAILED DESCRIPTION OF THE INVENTION

Figure 1:
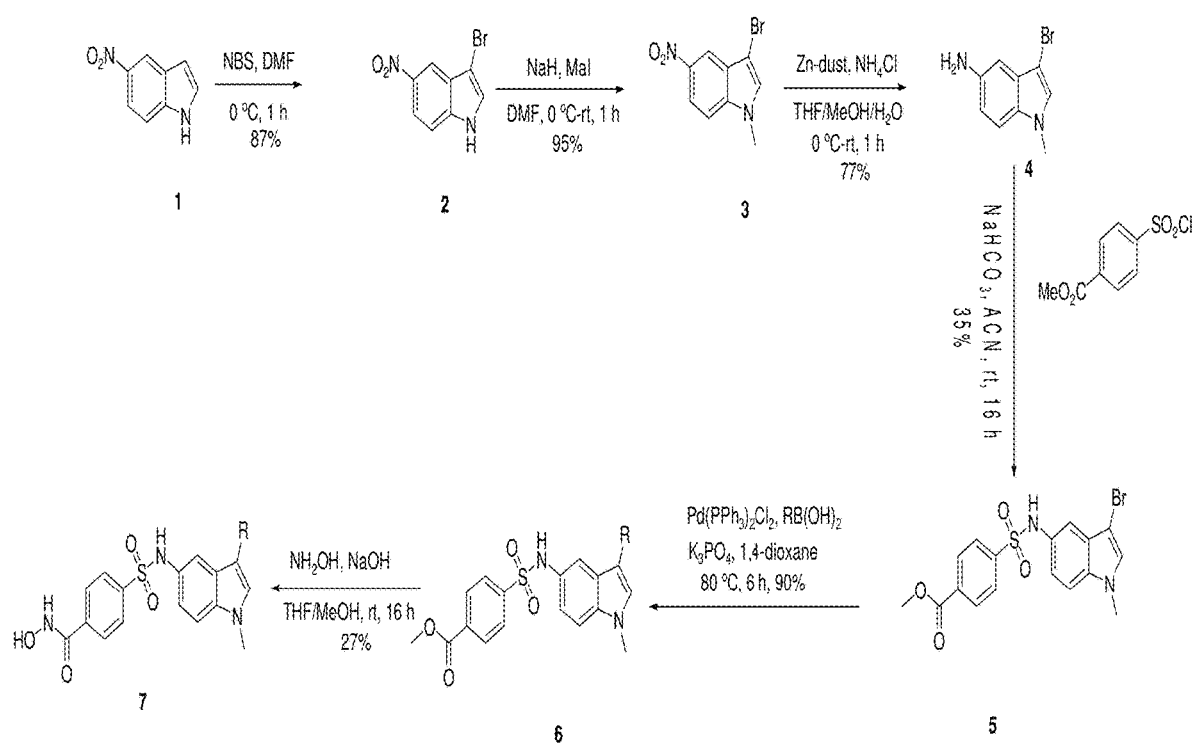
FIG. 1: synthesis of indole based sulfonyl hydroxamic acid

Sulfonyl hydroxamic acid derivatives are efficient structural motifs capable of showing diverse biological activities. This resulted in design and synthesis of a large number of Sulfonyl hydroxamic acid derivatives as illustrated in FIG. 1. These new class of sulfonyl hydroxamic acid derivatives are useful as selective HDAC inhibitors.

EXAMPLES

The present invention will be more specifically explained by following examples. However, the scope of the present invention is not limited to the scope of the examples stated below.

Step 1: Synthesis of 3-bromo-5-nitro-1H-indole

To a stirred solution of 5-nitro-1H-indole (1) (100 g, 0.61 mol) in DMF (1 L) was added NBS (131.1 g, 0.74 mol) at 0° C. and the solution was stirred for 1 h. After completion of reaction the mixture was diluted with cold water, filtered. The solid was washed with hexanes & product (130.0 g, 87%) used directly to the next step without further purification.

Step 2: Synthesis of 3-bromo-1-methyl-5-nitro-1H-indole

To a stirred solution of 3-bromo-5-nitro-1H-indole (2) (100.0 g, 0.414 mol) in DMF (1 L) was added NaH (19.9 g, 0.829 mol) at 0° C. and the solution was stirred for 0.5 h. Methyl iodide (87.7 g, 0.622 mol) was then added to the reaction mixture and the solution was stirred at RT for another 2 h. After completion of reaction the mixture was quenched with water and extracted with ethyl acetate. The organic extract was dried over anhydrous sodium sulphate, filtered and solvents evaporated from the filtrate under reduced pressure to obtain a crude, which was purified by column chromatography on silica gel (100-200 mesh), eluted with 10-15% gradient of EtOAc in pet-ether, to afford 3-bromo-1-methyl-5-nitro-1H-indole (101.0 g, 95%).

Step 3: Synthesis of 3-bromo-1-methyl-1H-indol-5-amine

To a stirred solution of 3-bromo-1-methyl-5-nitro-1H-indole (3) (7.0 g, 27.45 mmol) in THF:MeOH:$H_2O$ (1:1:1, 80 mL), were added Zn-dust (17.9 g, 274.5 mmol) & $NH_4Cl$ (14.8 g, 274.5 mmol) at 0° C. The reaction mixture was allowed to rt for 1 h. After completion of the reaction, the mixture was filtered through a celite bed & extracted with ethyl acetate. The organic extract was dried over anhydrous sodium sulphate, filtered and solvents evaporated from the filtrate under reduced pressure to obtain a crude (4.8 g, 77%) which was used directly to the next step without further purification.

Step 4: Synthesis of methyl 4-(N-(3-bromo-1-methyl-1H-indol-5-yl)sulfamoyl) benzoate To a stirred solution of 3-bromo-1-methyl-1H-indol-5-amine (4) (4.8 g, 21.3 mmol) in ACN (30 mL) were added $NaHCO_3$ (1.79 g, 21.3 mmol) & methyl 4-(chlorosulfonyl) benzoate (6.0 g, 25.5 mmol) at 0° C. and the solution was stirred at rt for 16 h. After completion of reaction the mixture was quenched with water and extracted with ethyl acetate. The organic extract was dried over anhydrous sodium sulphate, filtered and solvents evaporated from the filtrate under reduced pressure to obtain a crude, which was purified by column chromatography on silica gel (100-200 mesh), eluted with 0-40% gradient of EtOAc in pet-ether, to afford methyl 4-(N-(3-bromo-1-methyl-1H-indol-5-yl)sulfamoyl) benzoate (5) (3.2 g, 35%).

Step 5: Synthesis of methyl 4-(N-(1-methyl-3-aryl-1H-indol-5-yl)sulfamoyl)benzoate Phenyl boronic acid (0.90 mmol) was added to a solution of methyl 4-(N-(3-bromo-1-methyl-1H-indol-5-yl)sulfamoyl)benzoate (5) (0.4 mmol) in 1,4-dioxane (5 mL) followed by addition of $K_3PO_4$ (1.4 mmol) and the mixture was purged with argon for 20 min. $Pd(PPh_3)_2Cl_2$ (0.06 mmol) was added to the mixture purged another 5 min with argon, and heated at 80° C. for 6 h. After completion of the reaction, the mixture was cooled to ambient temperature and filtered through a celite bed. Solvents evaporated from the filtrate under reduced pressure and the crude obtained was purified by column chromatography on silica gel (100-200 mesh), to afford methyl 4-(N-(1-methyl-3-phenyl-1H-indol-5-yl)sulfamoyl)benzoate (6) (65-90%).

Step 6: Synthesis of N-hydroxy-4-(N-(1-methyl-3-aryl-1H-indol-5-yl)sulfamoyl) benzamide To a stirred solution of 50% aq. hydroxylamine (3 mL) & methyl 4-(N-(1-methyl-3-phenyl-1H-indol-5-yl)sulfamoyl)benzoate (6) (0.7 mmol) in THF:MeOH (1:1, 5 mL) was added 50% aq. KOH (0.5 mL) & the mixture was stirred at RT for 5 h. After completion of the reaction the solution was dried under vacuum. Resulting semi solid compounds was washed with ethyl acetate & diethyl ether to remove all nonpolar junk and to the residue was acidified with 0.1 N HCl. The solid appeared was collected by filtration & washed with water to obtain crude which was purified by column chromatography on silica gel (230-400 mesh) to afford N-hydroxy-4-(N-(1-methyl-3-aryl-1H-indol-5-yl)sulfamoyl)benzamide (15-45%).

Example 1: N-hydroxy-4-(N-(1-methyl-3-phenyl-1H-indol-5-yl)sulfamoyl)benzamide (1): $^1$H NMR (400 MHz, dmso) δ 11.35 (br s, 1H), 10.00 (br s, 1H), 9.19 (br s, 1H), 7.83-7.88 (m, 2H), 7.75 (d, J=8.31 Hz, 2H), 7.62-7.65 (m, 1H), 7.35-7.46 (m, 6H), 7.23 (td, J=4.40, 8.80 Hz, 1H), 6.94 (dd, J=1.96, 8.80 Hz, 1H), 3.77 (s, 3H). LC-MS purity: 97.29%; (ES$^+$): m/z 422.42 (M+H$^+$); tr=1.91 min.

Example 2: 4-(N-(3-(4-chlorophenyl)-1-methyl-1H-indol-5-yl)sulfamoyl)-N-hydroxy benzamide (2)

$^1$H NMR (400 MHz, dmso) δ 11.35 (br s, 1H), 10.02 (br s, 1H), 9.20 (br s, 1H), 7.80-7.87 (m, 2H), 7.72-7.80 (m, 2H), 7.69 (s, 1H), 7.36-7.50 (m, 6H), 6.94 (dd, J=1.71, 8.56 Hz, 1H), 3.77 (s, 3H). LC-MS purity: 98.81%; (ES$^+$): m/z 456.35 (M+H$^+$); tr=2.06 min.

Example 3: 4-(N-(3-(4-fluorophenyl)-1-methyl-1H-indol-5-yl)sulfamoyl)-N-hydroxy benzamide (3)

$^1$H NMR (400 MHz, dmso) δ 9.05-9.20 (br s, 3H), 7.85 (d, J=8.31 Hz, 2H), 7.75 (d, J=8.31 Hz, 2H), 7.62 (s, 1H), 7.35-7.44 (m, 4H), 7.26 (br t, J=8.80 Hz, 2H), 6.95 (s, 1H), 3.76 (s, 3H). LC-MS purity: 98.20%; (ES$^+$): m/z 440.38 (M+H$^+$); tr=1.95 min.

Example 4: 4-(N-(3-(3,4-dimethoxyphenyl)-1-methyl-1H-indol-5-yl)sulfamoyl)-N-hydroxy benzamide (4)

$^1$H NMR (400 MHz, dmso) δ 9.10-10.95 (m, 3H), 7.81-7.86 (m, 2H), 7.74 (d, J=8.31 Hz, 2H), 7.69 (br d, J=8.80 Hz, 1H), 7.57 (s, 1H), 7.45-7.48 (m, 1H), 7.35 (d, J=8.80 Hz, 1H), 6.93-7.06 (m, 3H), 6.89 (dd, J=1.71, 8.07 Hz, 1H), 3.79 (d, J=3.42 Hz, 6H), 3.75 (s, 3H). LC-MS purity: 95.57%; (ES$^+$): m/z 482.26 (M+H$^+$); tr=1.69 min.

Example 5: N-hydroxy-4-(N-(1-methyl-3-(naphthalen-1-yl)-1H-indol-5-yl)sulfamoyl) benzamide (5)

1H NMR (400 MHz, dmso) δ 11.34 (br s, 1H), 9.89 (br s, 1H), 9.23 (br s, 1H), 7.98 (d, J=7.82 Hz, 1H), 7.81-7.92 (m, 4H), 7.65-7.70 (m, 2H), 7.50-7.59 (m, 3H), 7.35-7.46 (m, 2H), 7.33 (d, J=6.36 Hz, 1H), 6.97-7.06 (m, 2H), 3.85 (s, 3H) LC-MS purity: 98.55%; (ES$^+$): m/z 472.42 (M+H$^+$); tr=2.08 min.

Example 6: N-hydroxy-4-(N-(1-methyl-3-(4-nitrophenyl)-1H-indol-5-yl)sulfamoyl) benzamide (6)

$^1$H NMR (400 MHz, dmso) δ 11.35 (br s, 1H), 10.14 (br s, 1H), 9.19 (s, 1H), 8.30 (br d, J=8.80 Hz, 2H), 7.98-8.04 (m, 1H), 7.81-7.88 (m, 2H), 7.69-7.81 (m, 4H), 7.60 (s, 1H), 7.44 (br d, J=8.80 Hz, 1H), 6.97 (br d, J=8.31 Hz, 1H), 3.81 (s, 3H). LC-MS purity: 97.55%; (ES$^+$): m/z 467.19 (M+H$^+$); tr=1.84 min.

Example 7: 4-(N-(3-(2,4-difluorophenyl)-1-methyl-1H-indol-5-yl)sulfamoyl)-N-hydroxy benzamide (7)

$^1$H NMR (400 MHz, dmso) δ 11.36 (br s, 1H), 9.99-10.05 (m, 1H), 9.86 (s, 1H), 7.71-7.87 (m, 2H), 7.55-7.68 (m, 2H), 7.28-7.46 (m, 3H), 7.13-7.28 (m, 2H), 6.85-6.98 (m, 1H), 3.79 (s, 3H). LC-MS purity: 96.17%; (ES$^+$): m/z 458.16 (M+H$^+$); tr=3.10 min.

Example 8: N-hydroxy-4-(N-(3-(2-methoxyphenyl)-1-methyl-1H-indol-5-yl)sulfamoyl) benzamide (8)

$^1$H NMR (400 MHz, dmso) δ 11.34 (br s, 1H), 9.95 (br s, 1H), 9.19 (br s, 1H), 7.81-7.87 (m, 2H), 7.73 (d, J=8.31 Hz, 2H), 7.50 (s, 1H), 7.31-7.35 (m, 1H), 7.18-7.28 (m, 3H), 7.06-7.11 (m, 1H), 6.98 (br t, J=7.34 Hz, 2H), 6.91 (dd, J=1.71, 8.56 Hz, 1H), 3.76 (s, 3H), 3.72 (s, 3H). LC-MS purity: 95.83%; (ES$^+$): m/z 450.46 (M–H$^+$); tr=4.05 min.

Example 9: N-hydroxy-4-(N-(3-(4-methoxyphenyl)-1-methyl-1H-indol-5-yl)sulfamoyl) benzamide (9)

$^1$H NMR (400 MHz, dmso) δ 11.39 (br s, 1H), 9.97 (br s, 1H), 9.21 (br s, 1H), 7.83-7.89 (m, 2H), 7.75 (d, J=8.31 Hz, 2H), 7.50-7.54 (m, 1H), 7.27-7.37 (m, 4H), 6.99 (d, J=8.80 Hz, 2H), 6.92 (dd, J=1.96, 8.80 Hz, 1H), 3.79 (s, 3H), 3.75 (s, 3H). LC-MS purity: 95.78%; (ES$^+$): m/z 452.22 (M+H$^+$); tr=1.83 min.

Example 10: N-hydroxy-4-(N-(3-(3-methoxyphenyl)-1-methyl-1H-indol-5-yl)sulfamoyl) benzamide (10)

$^1$H NMR (400 MHz, dmso) δ 11.33 (s, 1H), 10.02 (s, 1H), 9.16 (br s, 1H), 7.81-7.85 (m, 2H), 7.75 (d, J=8.80 Hz, 2H), 7.64-7.68 (m, 1H), 7.51 (d, J=1.96 Hz, 1H), 7.29-7.39 (m, 2H), 6.93-7.04 (m, 3H), 6.80 (dd, J=1.96, 8.31 Hz, 1H), 3.80 (s, 3H), 3.76 (s, 3H). LC-MS purity: 99.83%; (ES$^+$): m/z 452.16 (M+H$^+$); tr=1.84 min.

Example 11: 4-(N-(3-(3-chlorophenyl)-1-methyl-1H-indol-5-yl)sulfamoyl)-N-hydroxy benzamide (11)

$^1$H NMR (400 MHz, dmso) δ 11.32 (br s, 1H), 10.05 (br s, 1H), 9.16 (br s, 1H), 7.82-7.87 (m, 2H), 7.73-7.78 (m, 3H), 7.36-7.51 (m, 5H), 7.25-7.30 (m, 1H), 6.97 (dd, J=1.96, 8.80 Hz, 1H), 3.77 (s, 3H). LC-MS purity: 96.56%; (ES$^+$): m/z 454.16 (M+H$^+$); tr=2.0 min.

Example 12: N-hydroxy-4-(N-(1-methyl-3-(naphthalen-2-yl)-1H-indol-5-yl)sulfamoyl) benzamide (12)

$^1$H NMR (400 MHz, dmso) δ 11.35-11.94 (m, 2H), 9.19 (br s, 1H), 7.83-7.97 (m, 6H), 7.74-7.82 (m, 3H), 7.61-7.66 (m, 2H), 7.38-7.59 (m, 3H), 6.98 (dd, J=1.47, 8.80 Hz, 1H), 3.81 (s, 3H). LC-MS purity: 96.03%; (ES$^+$): m/z 472.22 (M+H$^+$); tr=2.06 min.

Example 13: 4-(N-(3-(3-chloro-4-fluorophenyl)-1-methyl-1H-indol-5-yl)sulfamoyl)-N-hydroxybenzamide (13)

$^1$H NMR (400 MHz, dmso) δ 11.17-11.70 (m, 2H), 9.18 (br s, 1H), 7.81-7.88 (m, 2H), 7.72-7.79 (m, 3H), 7.57-7.61 (m, 1H), 7.36-7.51 (m, 4H), 6.93-7.00 (m, 1H), 3.76 (s, 3H). LC-MS purity: 98.34%; (ES$^+$): m/z 474.13 (M+H$^+$); tr=2.02 min.

Example 14: 4-(N-(3-(2-fluorophenyl)-1-methyl-1H-indol-5-yl)sulfamoyl)-N-hydroxy benzamide (14)

$^1$H NMR (400 MHz, dmso) δ 11.31 (br s, 1H), 9.99 (br s, 1H), 9.17 (br s, 1H), 7.84 (br d, J=8.31 Hz, 2H), 7.74 (br d, J=8.31 Hz, 2H), 7.61 (s, 1H), 7.36-7.42 (m, 2H), 7.24-7.33 (m, 4H), 6.95 (br d, J=8.31 Hz, 1H), 3.79 (s, 3H). LC-MS purity: 95.81%; (ES$^+$): m/z 440.17 (M+H$^+$); tr=1.86 min.

Example 15: 4-(N-(3-(3-(benzyloxy)phenyl)-1-methyl-1H-indol-5-yl)sulfamoyl)-N-hydroxybenzamide (15)

$^1$H NMR (400 MHz, dmso) δ 11.32 (s, 1H), 10.03 (s, 1H), 9.16 (br s, 1H), 7.79-7.85 (m, 1H), 7.72-7.79 (m, 2H), 7.64-7.70 (m, 2H), 7.47-7.56 (m, 3H), 7.28-7.44 (m, 5H), 7.13-7.21 (m, 1H), 6.92-7.08 (m, 2H), 6.87 (br d, J=6.85 Hz, 2H), 5.14-5.20 (m, 2H), 3.72-3.79 (m, 3H). LC-MS purity: 95.36%; (ES$^+$): m/z 426.27 (M–H$^+$); tr=2.15 min.

Example 16: 4-(N-(3-(benzo[b]thiophen-3-yl)-1-methyl-1H-indol-5-yl)sulfamoyl)-N-hydroxybenzamide (16)

$^1$H NMR (400 MHz, dmso) δ 9.90 (br s, 1H), 8.01-8.08 (m, 1H), 7.80 (br d, J=7.82 Hz, 3H), 7.54-7.64 (m, 3H), 7.35-7.50 (m, 4H), 7.26-7.33 (m, 2H), 6.91 (br d, J=8.80 Hz, 1H), 3.77-3.84 (m, 3H). LC-MS purity: 99.75%; (ES$^+$): m/z 460.21 (M+H$^+$); tr=1.85 min.

Example 17: 4-(N-(3-(biphenyl-4-yl)-1-methyl-1H-indol-5-yl)sulfamoyl)-N-hydroxy benzamide (17)

$^1$H NMR (400 MHz, dmso) δ 11.37 (br s, 1H), 10.01 (br s, 1H), 9.18 (s, 1H), 7.85-7.90 (m, 2H), 7.69-7.80 (m, 7H), 7.46-7.54 (m, 5H), 7.34-7.41 (m, 2H), 6.96 (br d, J=8.80 Hz, 1H), 3.79 (s, 3H). LC-MS purity: 99.81%; (ES$^+$): m/z 478.08 (M+H$^+$); tr=2.02 min.

Example 18: N-hydroxy-4-(N-(1-methyl-3-(3-(trifluoromethyl)phenyl)-1H-indol-5-yl)sulfamoyl) benzamide (18)

$^1$H NMR (400 MHz, dmso) δ 10.46 (br s, 2H), 9.14 (br s, 1H), 7.71-7.86 (m, 7H), 7.66 (br t, J=7.82 Hz, 1H), 7.52-7.59 (m, 2H), 7.40 (d, J=8.80 Hz, 1H), 6.97 (dd, J=1.47, 8.80 Hz, 1H), 3.78 (s, 3H). LC-MS purity: 95.02%; (ES$^+$): m/z 490.14 (M+H$^+$); tr=2.05 min.

Biological Activity

Chemicals and Reagents: A biochemical assay was developed using luminescence based platform with 384 well-plate format. All recombinant enzymes HDAC6 (Cat No. BML-SE508-0050), HDAC8 (Cat No. BML-SE145-0100) and reference compound Trichostatin A (TSA, Cat No. BML-GR309-0005) were purchased from Enzo Life sciences. The HDAC-Glo™ I/II assay kit (Cat No. G6421) was purchased from Promega to measure the activity of HDAC class I and II inhibitor. An acetylated peptide was offered as an HDAC substrate in the kit. To perform the experiment Optiplate-384 well plates (Cat No. 6007299, from Perkin Elmer) were used.

Biochemical Assay

For screening HDAC inhibitors, dilutions of unknown compounds and the known HDAC inhibitor Trichostatin A were prepared as per the required concentrations in HDAC-Glo™ I/II Buffer. Final volume of diluted compound was kept 10 μl. HDAC enzymes were diluted using HDAC-Glo™ I/II buffer to the desired concentration (25 ng HDAC6 per well and 0.125U HDAC8 per well) and 10 μl of each HDAC enzyme was dispensed to each well of inhibitor dilutions. Enzyme and compound were incubated for 15 minutes at room temperature. HDAC Glo substrate vial was reconstituted with 10 mL of HDAC buffer and mixed with 10 μL developing reagent. 20 μL of prepared HDAC Glo reagent was added to each well and centrifuged the plate at room temperature for 30-60 seconds to ensure homogeneity. Plate was read at luminescence plate reader (EnVision® Multilabel Plate Reader from Perkin Elmer) after 15 minutes of incubation at room temperature. Generated data was exported to the excel file and data was analyzed using Graph Pad Prism to calculate IC50 value of the inhibitor.

Cell Based Screening

Cell culture & Reagents: All cell lines, used for the anti-proliferative screen, were obtained from American Type Culture Collection (ATCC). HeLa (Cervical cancer cell line), MCF-7 (Breast cancer cell line) and DU-145 (Prostate cancer cell line) were cultured in Dulbecco's modified Eagle's medium (DMEM, GIBCO), containing 10% fetal bovine serum (FBS; Life Technologies), penicillin and streptomycin (10,000 U/mL), at 37° C. and in 5% CO2. Cell Titer-Glo® Luminescent Cell Viability Assay kit (Cat No. G7573) was purchased from Promega to determine the number of viable cells in culture based on quantitation of the ATP present, which signals the presence of metabolically active cells.

Anti-Proliferative assay: For anti-proliferative screening, 2500 cells per well (For HeLa and DU-145 cell lines) and 5000 cells per well (for MCF-7 cell line) numbers of cells were seeded in a white opaque plate and incubated for 24 Hrs in 5% CO$_2$ incubator at 37° C. After 24 Hrs, compound dilutions were prepared as per the required concentrations in cell culture medium (DMEM) and diluted compounds were added and incubated with cells for 72 Hrs at 37° C. in 5% $CO_2$ incubator in the same 96 well-plate. After 72 Hrs, Cell Titer-Glo® reagent vial was reconstituted with 100 mL of Cell Titer Glo buffer and 100 μL of prepared reagent was added to each well. After incubating at room temperature for 30 minutes, luminescence was captured using luminescence plate reader (EnVision® Multilabel Plate Reader from Perkin Elmer). Generated data was exported to the excel file and data was analyzed using Graph Pad Prism to calculate IC50 value of the unknown inhibitor.

In Vitro ADME Screening

Hepatocytes Stability: Hepatocytes stability of test compounds was determined in human and mouse cryopreserved hepatocytes. 10 mM master stock of the test compound was prepared in DMSO. 1 mM working stock of test compound was prepared by diluting 20 μL of 10 mM stock in 180 μL of acetonitrile:Water (50:50). 2 μM of the final working stock was prepared by diluting 4 μL of 1 mM stock in 1996 μL of incubation medium. 200 μL of hepatocyte cell suspension (2×106 cells/mL) was added to 48-well plate and pre-incubated for 30 min at 37° C. in incubator. 200 μL of 2 μM working concentration of test compound was added to the cell suspension and incubated at 37° C. in incubator. Reaction was stopped at 0, 15, 30, 60, 90 and 120 minutes by precipitating 50 μL of the incubation mixture with 200 μL of acetonitrile containing internal standard. After precipitation samples were vortexed for 5 min at 1200 rpm and centrifuged at 4000 rpm for 10 min. Supernatant was transferred to analysis plate and diluted 2 fold with water and samples were analyzed on LC-MS/MS.

Permeability: Permeability of the test compounds was determined in Caco-2 cell monolayer (Cultured for 21 Days). 5 mL of 100 mM Sodium pyruvate, 5 mL of 100× non-essential amino acids, 5 mL of Pen-strep was added to 100 mL of heat inactivated fetal bovine serum to 385 mL of DMEM aseptically and mixed thoroughly. One vial of Hank's balanced salt (Sigma-H1387) was dissolved in 900 mL of milli Q water; adjusted the pH to 7.4 and made up the volume to 1000 mL with the same. The solution was filter sterilized and store at 4° C. 0.42 g of sodium hydroxide (Pellets), 3.95 g of monobasic potassium phosphate, and 6.18 g of sodium chloride were dissolved in 500 mL of purified water in a 1 L of volumetric container and pH was adjusted to exactly 7.4 using either 1N sodium hydroxide or 1N hydro chloride and made up the volume with water. In a 1 L volumetric flask, 2.24 g of Phares SIF Powder was dissolved in 500 mL of the FaSSIF Phosphate buffer at room temperature. Stirred at room temperature until the phares SIF Powder has dispersed and when a solution was obtained make up to volume (1 L) with the FaSSIF phosphate buffer. FaSSIF medium was allowed to equilibrate for 2 hours at ambient room temperature till opalescence. 10 mM stock solution of test compound was prepared in DMSO. 10 mM stock was diluted with FaSSIF Buffer to a final concentration of 10 μM. 250 μL of DMEM was added to the basal compartment of 96 well multi-screen Caco-2 plate and seeded 12000 cells/well (0.16×106 cells/mL) in all the apical wells required and one well with only media as blank without cells. Caco-2 plate was placed in $CO_2$ incubator at 37° C. for proliferation of cells.

On the day of assay, medium was removed and washed twice with HBSS Buffer and incubated with HBSS buffer for 30 minutes in an incubator and wells with TEER values greater than 230 ohm·cm$^2$ were selected for the incubation. 75 μL of test compound was added to apical wells and 250 μL of HBSS buffer with 2% BSA was added to basal wells. 25 μL of basal samples was collected at the specified time points (T=120 min) and diluted with 25 μL of FaSSIF buffer. 250 μL of test compound was added to basal wells and 75 μL of HBSS buffer with 2% BSA was added to apical wells. 25 μL of apical sample was collected at 120 min and diluted with 25 μL of FaSSIF buffer. Single point calibration curve in HBSS buffer with 2% BSA was used. Donor samples were diluted 1:1 with HBSS containing 2% BSA and receiver samples were diluted with 1.1 FaSSIF buffer and precipitated with 200 μL of acetonitrile containing internal standard and vortexed for 5 min at 1000 rpm, centrifuged at 4000 rpm for 10 min. 100 μL of supernatant was diluted with 200 μL of water and submitted for LC-MS/MS analysis.

Plasma Stability

Plasma stability of the test compounds was determined in mouse, human and rat plasma. 1 mM stock of test compound was prepared in Acetonitrile:water by diluting from 10 mM stock (i.e. 10 μL of 10 mM stock solution was added to 90 μL of Acetonitrile:water (50:50). 25 μM stock of test compound was prepared in Acetonitrile:water by diluting from 1 mM stock (i.e. 2.5 μL of 1 mM stock solution was added to 97.5 μL of Acetonitrile:water (50:50). The frozen mouse, rat and human plasma were thawed at room temperature and centrifuged at 1400×RCF 4° C., for 15 minutes. Approximately 90% of the clear supernatant fraction was transferred to a separate tube and was used for the assay. For 0 min samples, plasma was heat inactivated at 56° C. for 5 min. To 72 μL of heat inactivated plasma, 3 μL of 25 μM test compound was added. A 25 μL aliquot of the mixture was taken and crashed with 200 μL of acetonitrile containing internal standard and further processed along with other time points. For other time point samples, final working stock of 1 μM was prepared by diluting in plasma (i.e. 8 μL of 25 μM Acetonitrile:water stock was added to 192 μL of plasma). 200 μL of plasma containing the test compound was incubated for 120 min at 37° C. in shaker water bath with gentle shaking. 25 μL aliquot of sample at 60 and 120 min was precipitated immediately with 200 μL of acetonitrile containing internal standard and centrifuged at 4000×RCF, 4° C. for 20 minutes. 150 μL of supernatant was diluted with 150 μL of water and analyzed on LC-MS/MS.

Metabolic stability: Metabolic stability of the test compounds was determined in Human, Rat and mouse liver microsomes. 10 mM stock solution of test compound was prepared in DMSO and diluted with water:acetonitrile (1:1) to a concentration of 1 mM. Working concentration of 100 μM was prepared by further dilution with water:acetonitrile (1:1). 100 mL of Milli Q water was added to $K_2HPO_4$ (1.398 g) and $KH_2PO_4$ (0.27 g) to get final pH 7.4. 2.5 μL test compound was pre incubated for 10 minutes at 37° C. with 75 μL HLM or RLM or MLM at 3.33 mg per mL and 85 μL of 100 mM potassium phosphate buffer. 32.5 μL of pre incubated mixture was incubated for 60 minutes without cofactor (NADPH) at 37° C. with 17.5 μL of 100 mM potassium phosphate buffer. For 0 minute sample, 16.25 μL of pre-incubated mixture was added to 200 μL of acetonitrile containing internal standard and 8.75 μL of cofactor (NADPH). 62 μL of cofactor (NADPH, 2.5 mM) was added to remaining incubation mixture and Incubated for 60 minutes at 37° C. 25 μL incubation mixtures was added to 200 μL of acetonitrile containing internal standard, vortexed for 5 minutes at 1200 rpm and centrifuged for 10 min at 4000 rpm. Supernatant diluted 2 fold with water and injected and analyzed on LC-MS/MS.

Pharmacokinetic Study: Sprague-Dawley (SD) male rats were used for the pharmacokinetic study of the test compound. Single dose of test compound 1 mg/kg was used with a dose volume of 5 mL/kg and dose concentration of 0.2 mg/mL for intravenous route of administration. Similarly for per oral and sub cutaneous route of administration, 10 mg/kg dose with a dose volume of 5 mL/kg and dose concentration of 2 mg/mL was used. Test compound was prepared in different vehicles for different route of administration. For intravenous and subcutaneous route of administration, DMSO (5%), 15% PEG-400 in water (95%) was used as a vehicle control. 0.2% tween 80, 0.4% HPMC in water was used as vehicle control for preparing test compound to inject subcutaneously. Samples were collected at different time points and analyzed by using bio analytical method.

Results and Discussion

- HDAC6 and HDAC8 assays were developed successfully in both Fluorescence and Luminescence assay format.
- Testing of compounds was done in the luminescence assay to support SAR.
- Cell based assay optimization was performed on cancerous cell lines like HeLa, DU145, MCF-7 and SKOV3 to test the anti-proliferative activity of the compounds.
- Established Pan-HDAC (Rat Liver) assay to test the potency of the compounds on other HDACs.
- HeLa cells nuclear extract assay was developed to check the activity of those compounds which are not active in the cell based assays.
- Key compounds have been screened for ADME and PK Comparison of SAHA and TSA in HDAC6 and HDAC8 Biochemical Assay Test compounds were screened against HDAC6 and HDAC8 with full DRC to get the accurate IC50 values.

IC50 values (nM) for TSA, SAHA and Puromycin on cancerous cell lines HeLa (Cervical cancer cells), MCF-7 (Breast cancer cells), DU-145 (Prostate cancer cells) and SKOV3 (Ovarian cancer cells) in cell based assays are tabulated in Table 1:

TABLE 1

IC50 values (nM) for TSA, SAHA and Puromycin against human cancer cell lines

| Compounds | HeLa cells | MCF-7 cells | DU-145 cells | SKOV3 cells |
|---|---|---|---|---|
| TSA | 124 | 153 | 539 | 242 |
| SAHA | 2391 | 613 | 796 | 1395 |
| PUROMYCIN | 619 | 408 | 967 | 296 |

Based on the data, it was decided to use either Puromycin or TSA as a reference molecule for the proliferation assay. SAHA molecule was not very potent compound and IC50 was observed in micro molar range.

Biochemical IC50 (nM) and cell based IC50 (µM) values of selected key test compounds using 4 cancerous cell lines HeLa (cervical cancer cells), MCF-7 (Breast cancer cells), DU-145 (Prostate cancer cells), SKOV3 (Ovarian cancer cells) and Non-cancerous cell line AD293 and data tabulated in Table 2:

TABLE 2

Biochemical IC50 (nM) and cell based IC50 (µM) values of representative compounds against human cancer cell lines

| | Cell line used | | | | | Bio-chemical Assay | |
|---|---|---|---|---|---|---|---|
| | HeLa | MCF-7 | DU-145 | SKOV3 | AD293 | IC50, Nm | |
| Cpd ID | IC50, µM | | | | | HDAC6 | HDAC8 |
| BIRAC-91 | 2.8 | 4.7 | 2.8 | 1.7 | 12.5 | 1480 | 11.9 |
| BIRAC-93 | 0.9 | 2.4 | 1.0 | 1.6 | 14.7 | 738 | 14.9 |
| BIRAC-106 | 0.9 | 1.7 | 1.2 | 1.5 | 14.4 | 357 | 15.3 |
| BIRAC-107 | 0.9 | 1.9 | 1.0 | 1.9 | 14.5 | 336 | 8.8 |
| BIRAC-108 | 3.3 | 3.1 | 1.3 | 1.8 | 16.4 | 539 | 27 |
| BIRAC-127 | 0.9 | 1.5 | 1.9 | 0.6 | 11.0 | 917 | 258 |
| Cpd ID | IC50, µM | | | | | | |
| TSA | 124 | 153 | 539 | 242 | | 0.9 | 98 |
| SAHA | 2391 | 613 | 796 | 1395 | | 245 | 3676 |
| Puromycin | 387.0 | 254.0 | 382.0 | 296.0 | | | |

Figure 2:
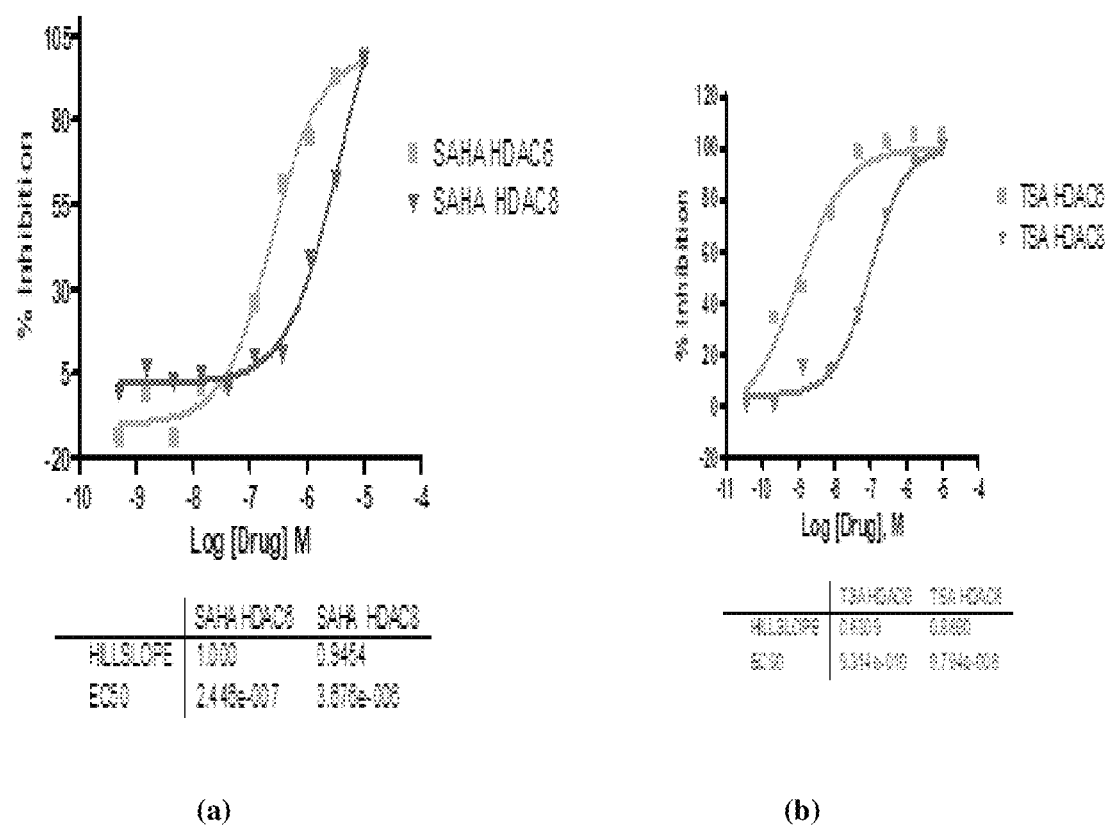
FIG. 2: Comparison of SAHA [a] and TSA [b] in HDAC6 and HDAC8 biochemical assay

Screening results for all compounds tested against HDAC6 and HDAC8 are given below. TSA and SAHA known drugs were used for screening against HDAC6 and HDAC8 are shown in FIG. 2.

SAHA and TSA (Trichostatin A) compounds have been used as a known reference compounds in biochemical assay. As TSA was more potent than SAHA and used as an assay control for all the biochemical assays. Further, in comparison to SAHA, TSA was 270 fold and 38 fold more selective to HDAC6 and HDAC8 respectively.

Comparison of SAHA, TSA and Puromycin in Different Cancer Cell Lines (HeLa, DU-145, MCF-7 and SKOV3)

Figure 3:
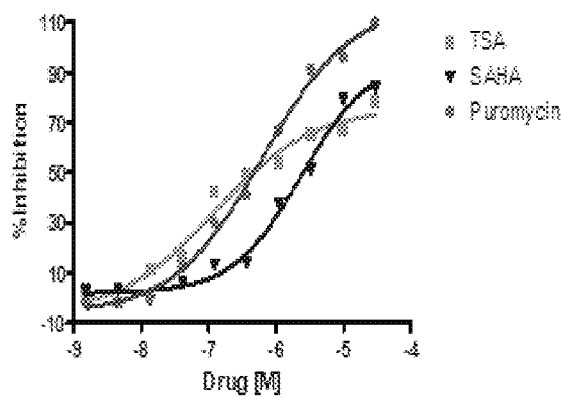
FIG. 3: Comparison of SAHA, TSA and Puromycin in HeLa [a], DU-145 [b], MCF-7 [c] and SKOV3 [d] cell lines
Figure 3:
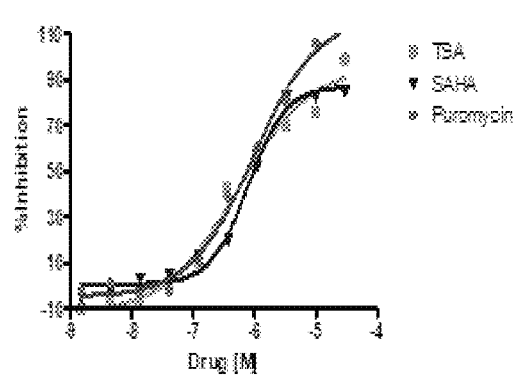
Figure 3:
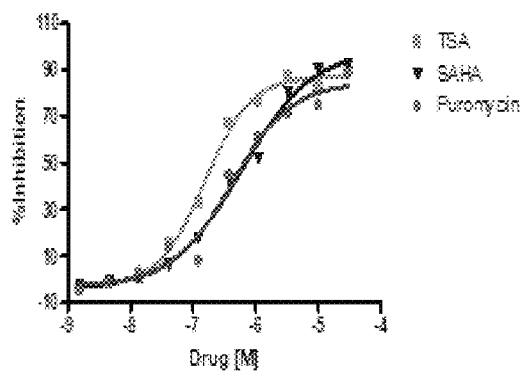
Figure 3:
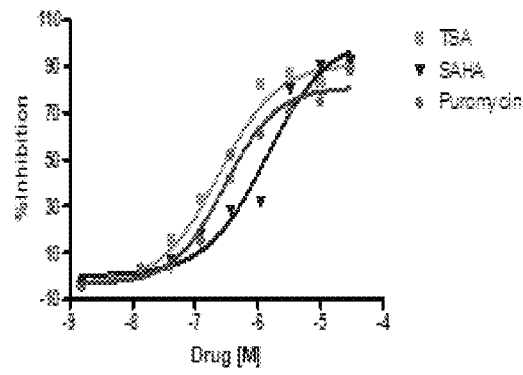

Compounds were screened against different cancer cell lines [HeLa, DU-145, MCF-7 and SKOV3] for anti-proliferative activity using luminescence based cell proliferation assay using Promega Glo kit are shown in FIG. 3.

Key compounds have been tested against cancer cell lines along with AD293 cells (Non-cancerous) and showed anti-proliferative activity against cancer cells but did not show anti-proliferative activity against AD293 cells.

For cell based assays, 30 µM was used as a top concentration for compound screening. If compounds do not show inhibition at 30 µM, this is being considered as non-toxic concentration and showed no cell proliferation.

HDAC selectivity data for selected test compounds against HDAC1, HDAC2, HDAC3, HADC10 and HDAC11 in biochemical assay.

Selected compounds were also screened against a panel of HDACs (includes HDAC1, HDAC2, HADC3, HDAC10 and HDAC11) to check the selectivity of the compound and data tabulated in table 3.

TABLE 3

| | IC50 (nM) values of representative compounds against HDACs | | | | | | |
|---|---|---|---|---|---|---|---|
| | COMPOUND | | | | | | |
| CODE | HDAC1 IC50 nm | HDAC2 IC50 nm | HDAC3 IC50 nm | HDAC10 IC50 nm | HDAC11 IC50 nm | HDAC6 IC50 nm | HDAC8 IC50 nm |
| BIRAC91 | 1270 | 1740 | 2200 | 681 | 4600 | 1480 | 11.9 |
| BIRAC95 | 5970 | <10000 | >10000 | 3400 | >10000 | 3320 | 34 |
| BIRAC108 | 177 | 822 | 2230 | 463 | 512 | 539 | 27 |
| BIRAC127 | 345 | 929 | 979 | 2610 | 534 | 917 | 258 |

BIRAC-108 was more selective to HDAC-8 and almost 80 folds less selective to HDAC-3; Reference compound TSA (Trichostatin A) was non selective to HDAC and has very good potency for all HDACs.

Advantages of the Invention

The advantages of the method are given below.

1. The main advantage of the present invention is that it provides novel sulfonyl hydroxamic acids derivatives.
2. The advantage of the present invention is that it provides an efficient process for the preparation of diversely substituted novel sulfonyl hydroxamic acid derivatives.
3. The process for the synthesis of these new sulfonyl hydroxamic acid derivatives involves operationally simple and highly efficient synthetic protocol giving rise to the desired products in high yields.
4. Another advantage of the present invention is the use of these sulfonyl hydroxamic acid compounds as HDAC inhibitors.

The invention claimed is:

1. A sulfonyl hydroxamic acid compound of general formula I:

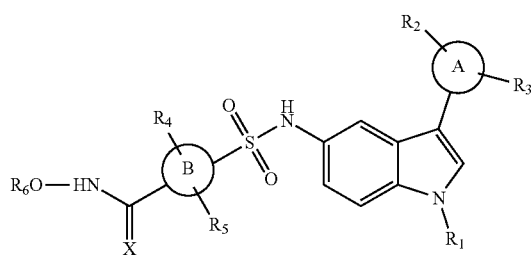

wherein:
X is O,
ring A and B are aryl, heteroaryl, cycloalkyl, fused aryl or fused alkyl group, and
$R_1$, $R_2$, $R_3$, $R_4$, $R_5$, and $R_6$ are hydrogen, alkoxy, aryloxy, hydroxy, ester, amide, amino, alkyl, aryl, heteroaryl, halogen, hydroxy, alkoxy, aryloxy, nitro, cyano, ester, or aldehyde.

2. The sulfonyl hydroxamic acid compound as claimed in claim 1, selected from the group consisting of:

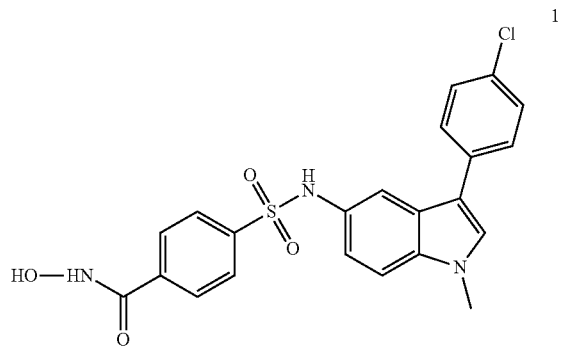

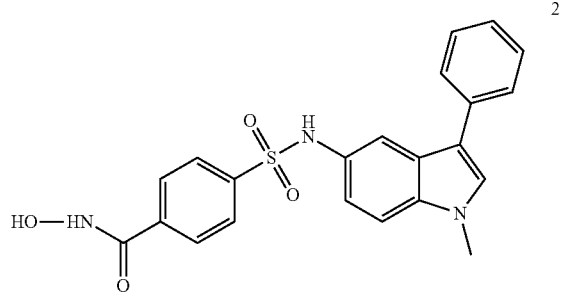

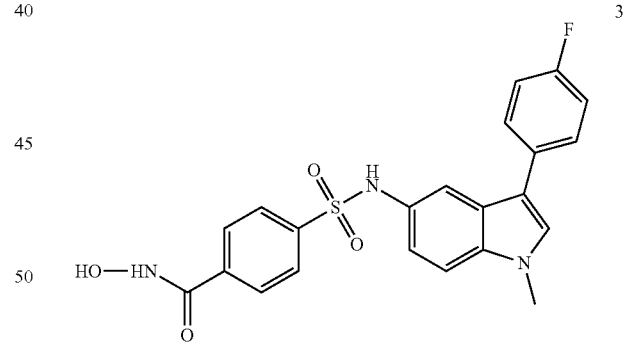

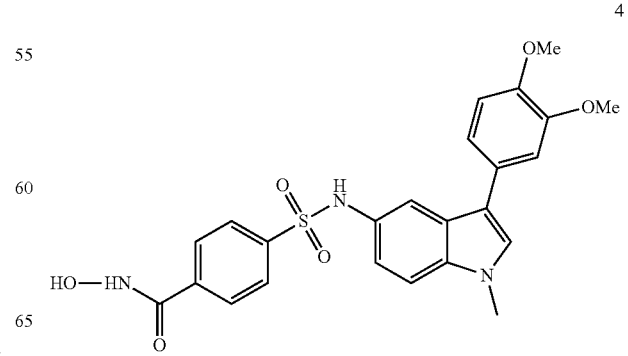

-continued
5
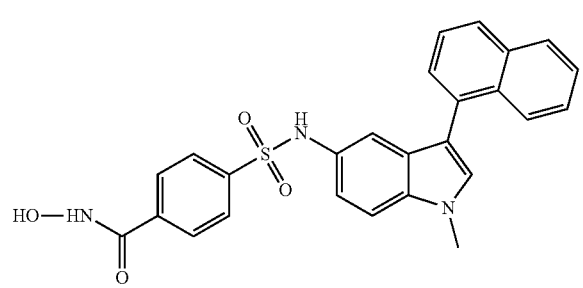
6
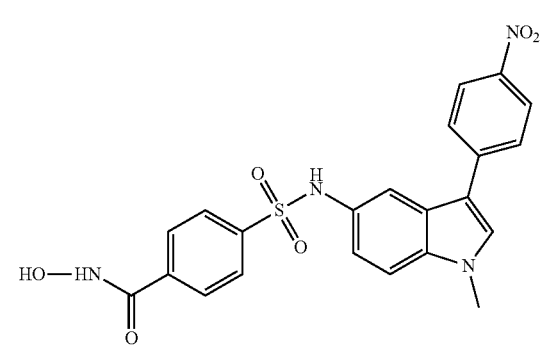
7
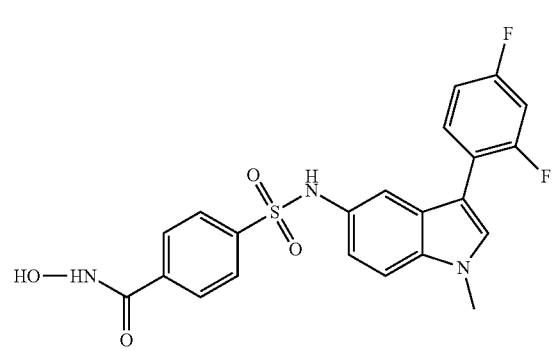
8
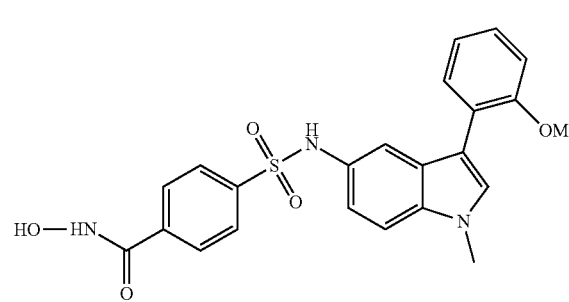
9
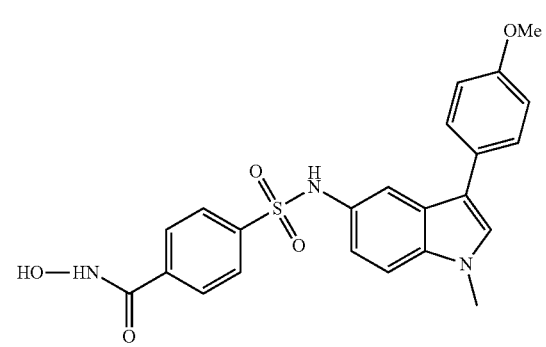
-continued
10
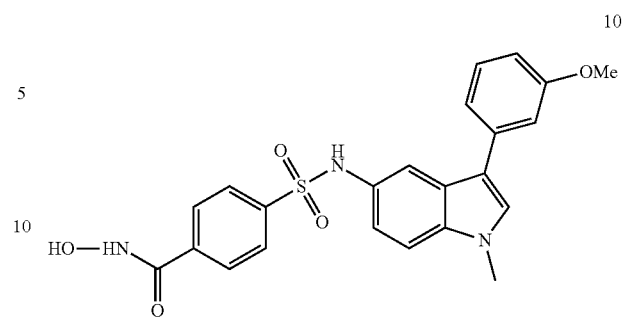
11
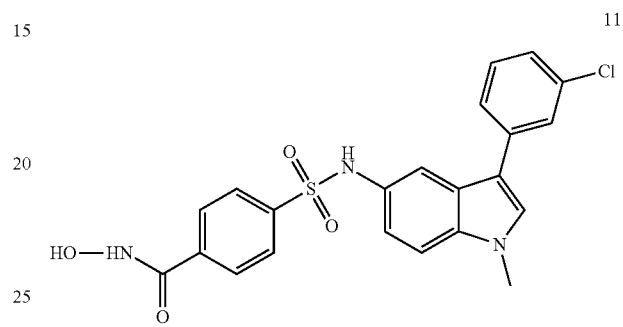
12
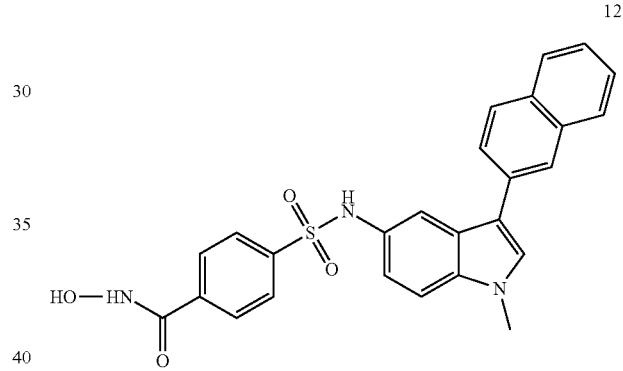
13
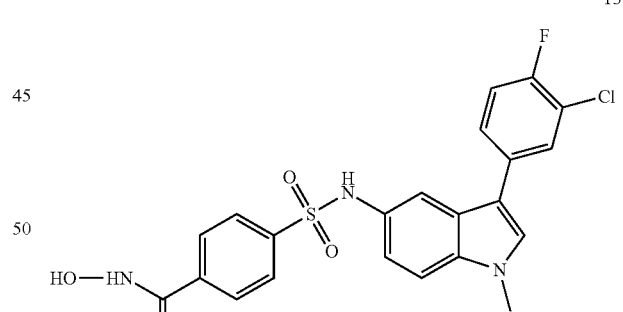
14
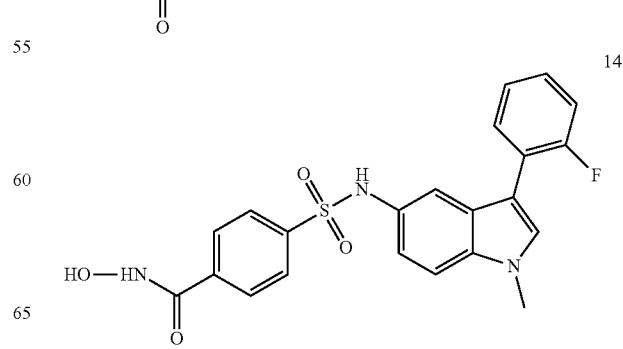

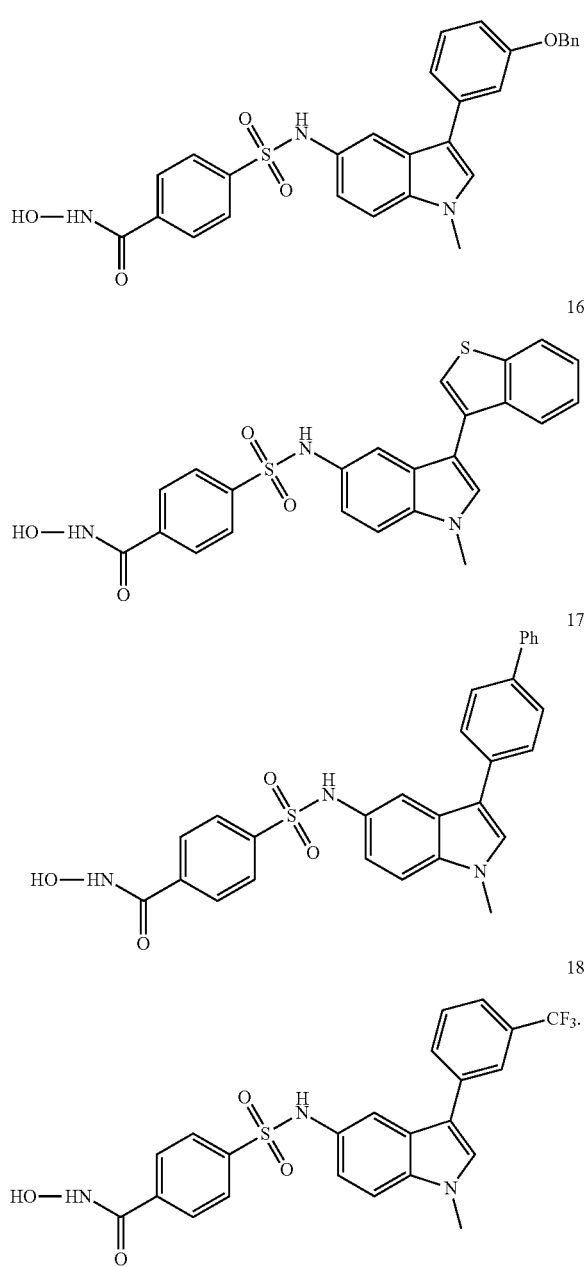

3. The sulfonyl hydroxamic acid compound as claimed in claim 1, wherein the sulfonyl hydroxamic acid compounds are represented by:

N-hydroxy-4-(N-(1-methyl-3-phenyl-1H-indol-5-yl)sulfamoyl)benzamide (1), 4-(N-(3-(4-chlorophenyl)-1-methyl-1H-indol-5-yl)sulfamoyl)-N-hydroxybenzamide (2), 4-(N-(3-(4-fluorophenyl)-1-methyl-1H-indol-5-yl)sulfamoyl)-N-hydroxybenzamide (3), 4-(N-(3-(3,4-dimethoxyphenyl)-1-methyl-1H-indol-5-yl) sulfamoyl)-N-hydroxy benzamide (4), N-hydroxy-4-(N-(1-methyl-3-(naphthalen-1-yl)-1H-indol-5-yl)sulfamoyl)benzamide (5), N-hydroxy-4-(N-(1-methyl-3-(4-nitrophenyl)-1H-indol-5-yl)sulfamoyl)benzamide (6), 4-(N-(3-(2,4-difluorophenyl)-1-methyl-1H-indol-5-yl) sulfamoyl)-N-hydroxybenzamide (7), N-hydroxy-4-(N-(3-(2-methoxyphenyl)-1-methyl-1H-indol-5-yl)sulfamoyl)benzamide (8), N-hydroxy-4-(N-(3-(4-methoxyphenyl)-1-methyl-1H-indol-5-yl)sulfamoyl)benzamide (9), N-hydroxy-4-(N-(3-(3-methoxyphenyl)-1-methyl-1H-indol-5-yl)sulfamoyl)benzamide (10), 4-(N-(3-(3-chlorophenyl)-1-methyl-1H-indol-5-yl)sulfamoyl)-N-hydroxybenzamide (11), N-hydroxy-4-(N-(1-methyl-3-(naphthalen-2-yl)-1H-indol-5-yl)sulfamoyl)benzamide (12), 4-(N-(3-(3-chloro-4-fluorophenyl)-1-methyl-1H-indol-5-yl)sulfamoyl)-N-hydroxybenzamide (13), 4-(N-(3-(2-fluorophenyl)-1-methyl-1H-indol-5-yl)sulfamoyl)-N-hydroxybenzamide (14), 4-(N-(3-(3-(benzyloxy)phenyl)-1-methyl-1H-indol-5-yl) sulfamoyl)-N-hydroxybenzamide (15), 4-(N-(3-(benzo[b]thiophen-3-yl)-1-methyl-1H-indol-5-yl) sulfamoyl)-N-hydroxybenzamide (16), 4-(N-(3-(biphenyl-4-yl)-1-methyl-1H-indol-5-yl)sulfamoyl)-N-hydroxybenzamide (17), and N-hydroxy-4-(N-(1-methyl-3-(3-(trifluoromethyl)phenyl)-1H-indol-5-yl) sulfamoyl) benzamide (18).

4. A process for the preparation of a sulfonyl hydroxamic acid compound as claimed in claim 1 comprising the steps of:
a) brominating nitroindole using NBS in a polar non-protonated solvent at −5 to 5° C. for 40-100 minutes;
b) protecting indole NH using alkyl halides and hydride base in a polar non-protonated solvent at −5 to 5° C. for 40-100 minutes;
c) reducing nitro group to amine using Zn dust in a polar solvent mixture at −5 to 5° C. for 40-100 minutes;
d) base-mediated coupling between sulfonyl and amine functionalities in a polar solvent at 25-40° C. for 12-24 hours;
e) suzuki reaction/coupling using boronic acid derivative, palladium catalyst and phosphate salt in a polar solvent at 70-100° C. for 5-10 hours; and
f) installing hydroxamic acid using a hydroxy amine and a base in polar solvent mixture at 25-40° C. for 12-24 hours.

5. The process as claimed in claim 4, wherein brominating reagent is selected from Bromine ($Br_2$) or N-bromosuccinimide (NBS).

6. The process as claimed in claim 4, wherein polar non-protonated solvent is selected from Dimethylformamide (DMF) or Dimethyl sulfoxide (DMSO).

7. The process as claimed in claim 4, alkyl halide is selected from methyl iodide, methyl bromide, ethyl iodide or ethyl bromide.

8. The process as claimed in claim 4, wherein hydride base is selected from Sodium hydride (NaH), Potassium hydride (KH) or Caesium hydride (CsH).

9. The process as claimed in claim 4, wherein metal reducing reagent is selected from Zinc (Zn) or Iron (Fe).

10. The process as claimed in claim 4, wherein polar solvent is selected from tetrahydrofuran (THF), methanol (MeOH), ethanol (EtOH), water ($H_2O$), acetonitrile ($CH_3CN$), 1,4-dioxan or diethyl ether ($Et_2O$).

11. The process as claimed in claim 4, wherein base is selected from Sodium hydroxide (NaOH), potassium hydroxide (KOH), caesium hydroxide (CsOH), Sodium bicarbonate ($NaHCO_3$) or potassium bicarbonate ($KHCO_3$).

12. The process as claimed in claim 4, wherein boronic acid derivative is selected from aryl or heteroaryl or cycloalkyl or fused aryl or fused alkyl group with substitutions $R_1$ and/or $R_2$, where $R_1$ and/or $R_2$ is hydrogen, alkoxy, aryloxy, hydroxy, ester, amide, amino, alkyl, aryl, heteroaryl, halogen, hydroxy, alkoxy, aryloxy, nitro, cyano, ester or aldehyde.

13. The process as claimed in claim 4, wherein palladium catalyst is selected from Bis(triphenylphosphine)palladium (II) dichloride $(Pd(PPh_3)_2Cl_2)$ or Tetrakis(triphenylphosphine)palladium $(Pd(PPh_3)_4)$.

14. The process as claimed in claim 4, wherein phosphate salt is selected from potassium phosphate $(K_3PO_4)$ or Sodium phosphate $(Na_3PO_4)$.

15. A method of selectively inhibiting a histone deactylase (HDAC) comprising exposing the HDAC to a sulfonyl hydroxamic acid compound as claimed in claim 1.

\* \* \* \* \*